United States Patent
Hong et al.

(10) Patent No.: US 11,858,873 B2
(45) Date of Patent: Jan. 2, 2024

(54) METHOD FOR CONTINUOUSLY SYNTHESIZING PROPELLANE COMPOUND

(71) Applicant: JILIN ASYMCHEM LABORATORIES CO., LTD., Jilin (CN)

(72) Inventors: Hao Hong, Morrisville, NC (US); Enxuan Zhang, Tianjin (CN); Jiangping Lu, Tianjin (CN); Fuliang Wei, Tianjin (CN); Sihang Yang, Tianjin (CN)

(73) Assignee: JILIN ASYMCHEM LABORATORIES CO., LTD., Jilin (CN)

( * ) Notice: Subject to any disclaimer, the term of this patent is extended or adjusted under 35 U.S.C. 154(b) by 0 days.

(21) Appl. No.: 17/620,268

(22) PCT Filed: Jun. 18, 2019

(86) PCT No.: PCT/CN2019/091732
§ 371 (c)(1),
(2) Date: Dec. 17, 2021

(87) PCT Pub. No.: WO2020/252661
PCT Pub. Date: Dec. 24, 2020

(65) Prior Publication Data
US 2022/0380273 A1    Dec. 1, 2022

(51) Int. Cl.
*C07C 1/28* (2006.01)

(52) U.S. Cl.
CPC .......... *C07C 1/28* (2013.01); *C07C 2531/12* (2013.01)

(58) Field of Classification Search
CPC ...................................... C07C 1/28
See application file for complete search history.

(56) References Cited

U.S. PATENT DOCUMENTS 4,436,937 A * 3/1984 Baardman ............. C07C 275/28
564/409

FOREIGN PATENT DOCUMENTS

WO    WO-2017157932 A1 *  9/2017  .............. C07C 1/28
WO    WO-2019051038 A1 *  3/2019  ............ B01J 19/002

OTHER PUBLICATIONS

Meijere et al. "Product Class 2: Cyclopropanes" Sciend of Synthesis 48. 2009. pp. 477-613 (Year: 2009).*
University of Michigan "Continuous Stirred Tank Reactors" pp. 1-3. 2017 (Year: 2017).*
Belzner et al., 1988, "Concerning the Synthesis of [1.1.1]Propellane", 122:397-398.
International Search Report for PCT/CN2019/091732, dated Mar. 2020.
Jiang et al. "Chemical Technology Inorganic Section", Higher Education Press, Apr. 30, 1988, p. 17-18.
Rehm et al., 1999, "A Facile Route to Bridgehead Disubstituted Bicyclo[1.1.1]pentanes Involving Palladium-Catalyzed Cross-Coupling Reactions", 2079-2085.
Semmler et al., 1985, "Tetracyclo[5.1.0.0.0]octane, a [1.1.1]Propellane Derivative, and a New Route to the Parent Hydrocarbon", 107:6410-6411.
Written Opinion for PCT/CN2019/091732, dated Mar. 2020.
Chemical Engineering Manual, the 6th Edition of Revision, 2001, 186-187.
Extended European Search Report for European Patent Application No. 19 933 598.5 dated Dec. 12, 2022.
First Examination Report for Indian Patent Application No. 202117060930 dated Jul. 6, 2022.
Office Action for Japanese Patent Application No. 2021572331A dated Dec. 2022.
Werner et al., 1996, "Synthesis of [1.1.1] Propellanes by Bridging of Bicyclo[1.1.0]butanes", Liebigs Ann. 1705-1715.

* cited by examiner

*Primary Examiner* — In Suk C Bullock
*Assistant Examiner* — Alyssa L Cepluch
(74) *Attorney, Agent, or Firm* — Riverside Law LLP

(57) ABSTRACT

Disclosed is a method for continuously synthesizing a propellane compound. The method includes the following steps: using 1,1-dibromo-2,2-bis(chloromethyl)cyclopropane or a derivative thereof as a raw material to form a ring with a lithium metal agent by a continuous reaction, so as to synthesize the propellane compound. A technical scheme of the present disclosure is applied, and a continuous reaction device is used.

7 Claims, No Drawings

METHOD FOR CONTINUOUSLY SYNTHESIZING PROPELLANE COMPOUND

CROSS-REFERENCE TO RELATED APPLICATIONS

This application is a U.S. National Phase application filed under 35 U.S.C. § 371 claiming benefit to International Patent Application No. PCT/CN2019/091732, which was filed on Jun. 18, 2019, the entire contents of which are incorporated herein by reference in its entirety.

TECHNICAL FIELD

The present disclosure relates to the field of medicines and chemical industries, and in particular to a method for continuously synthesizing a propellane compound.

BACKGROUND

Propellane is an important bioisostere (Stepan, A. F.; Subramanyam, C.; Efremov, I. V.; Dutra, J. K.; O'Sullivan, T. J.; Dirico, K. J.; McDonald, W. S.; Won, A.; Dorff, P. H.; Nolan, C. E.; Becker, S. L.; Pustilnik, L. R.; Riddell, D. R. Kauffman, G. W.; Kormos, B. L.; Zhang, L.; Lu, Y.; Capetta, S. H.; Green, M. E.; Karki, K.; Sibley, E.; Atchison, K. P.; Hallgren, A. J.; Oborski, C. E.; Robshaw, A. E.; Sneed, B.; O'Donnell, C. J. J. Med. Chem. 2012, 55, 3414), with the reduced number of carbon atoms in three bridge chains, a molecular framework becomes more "stiff", the tension is much greater than that of a corresponding bicyclic compound, and the thermodynamic and kinetic stability is also reduced. Therefore, it has the special activity (Burkhard, J. A.; Guerot, C.; Knust, H.; Carreira, E. M. Org. Lett. 2012). It is verified that after a phenyl derivative is replaced with the propellane, it greatly improves the permeability, water solubility, and metabolic stability of a drug molecule (Westphal, M. V.; Wolfstädter, B. T.; Plancher, J. M.; Gatfield, J.; Carreira, E. M. ChemMedChem 2015, 10, 461~469). In addition, some researches show that bicyclopentyl[1.1.1] may increase the cubic tropism of the molecule and may be used as a rigid spacer in the drug molecule for regulating distance and configuration between groups, many propellane substitute drugs are successfully explored in the field of pharmaceutical market at present, such as a depression inhibitor, a bacteriostatic agent, an atypical PKC inhibitor, and a heat shock protein inhibitor. (Kolb, H C; Finn, M G; Sharpless, K B Angew. Chem., Int. Ed. 2001, 40, 2004~2021).

Propellane derivatives, such as 3-aminobicyclo[1.1.1] pentane-1-formic acid, have great potential in the field of medicinal chemistry researches as an unnatural amino acid (Patzel, M.; Sanktjohanser, M.; Doss, A.; Henklein, P.; Eur. J. Org. Chem. 2004, 493), but due to the complicated synthesis process, the cost is very high (a methyl ester derivative is ~$300,000/kg). So far, there are only a few reports on the synthesis of such compounds. Kevin Bunker and others of the La Jolla Laboratory in the United States synthesize a BCP-amine derivative through a hydrogen ammonification reaction of [1.1.1] propellane (Waser, J.; Gaspar, B.; Nambu, H.; Carreira, E. M. J. Am. Chem. Soc. 2006, 128, 11693; Bunker, K. D.; Sach, N. W.; Huang, Q.; Richardson, P. F. Org. Lett. 2011, 13, 4746. For syntheses of BCP-amine other than ref 1c, 1d, and 11a, see: Bunker, K. D. Patent WO 2015/089170 A1), Professor Phil Baran of the Scripps Research Institute adopts a strategy of ring tension release, and performs nucleophilic ring-opening on the [1.1.1] propellane through a Turbo amino Grignard reagent so as to synthesize a target product (Spangler, J E; Zhu, H.; Zhu, J.; Baran, P S J Am. Chem. Soc. 2017, 139, 3209). In addition, Professor Paul Knochel of the University of Munich also synthesizes a bis-arylated BCP derivative through a similar pathway (Makarov, I S; Brocklehurst, C E; Karaghiosoff, K.; Koch, G.; Knochel, P. Angew. Chem. Int. Ed. 2017, 56, 12774). Recently, researchers such as Junichiro Kanazawa and Masanobu Uchiyama, of Rlkagaku KENkyusho/Institute of Physical and Chemical Research (RIKEN) start from the [1.1.1]propellane, and achieve the efficient synthesis of a 3-substituted BCP-amine derivative through a Fe-catalyzed multi-component radical carbon amination process (Junichiro Kanazawa, Katsuya Maeda, and Masanobu Uchiyama J. Am. Chem. Soc, 2017, 139, 17791).

According to existing document reports, synthesis methods for the propellane are mainly divided into two categories. One is that an expensive raw material of dibromo or diiodobicyclo[1,1,1]pentane is used, and under the action of strong base t-butyl lithium, the propellane is synthesized by cycle-closing (Wiberg, K. B.; Walker, F. H.; Journal of the American Chemical Society; vol. 104; (1982); 523; Wiberg, Kenneth B.; McMurdie, Neil; Journal of the American Chemical Society; vol. 113; 23; (1991); 8995~8996), reaction conditions are harsh, the yield is lower, and the reaction stability is poor; and the other is that 1,1-dibromo-2,2-chloromethyl cyclopropane (Elliott, Luke D.; Knowles, Jonathan P.; Koovits, Paul J.; Maskill, Katie G.; Ralph, Michael J.; Lejeune, Guillaume; Edwards, Lee J.; Robinson, Richard I.; Clemens, Ian R.; Cox, Brian; Pascoe, David D.; Koch, Guido; Eberle, Martin; Berry, Malcolm B.; Booker-Milburn, Kevin I.; Chemistry—A European Journal; vol. 20; 46; (2014); 15226~15232; Rehm, J. D. Daniel; Ziemer, Burghard; Szeimies, Guenter; European Journal of Organic Chemistry; 9; (1999); 2079~2085) is used as a raw material, under the action of excessive methyl lithium, the propellane is prepared by two times of cycle-closing in the molecule, disadvantages are that a large amount of a methane gas is produced in a process and the reaction is uncontrollable. Both methods require the use of an active metal reagent. However, it is indicated from a destruction experiment that the propellane is decomposed in different degrees under aqueous solution, acidity and alkaline conditions, this is the biggest bottleneck of the scale-up preparation thereof. At present, the synthesis of the propellane is also on a small scale in a laboratory, so the application of the propellane is greatly limited.

In general, the traditional synthesis of the propellane compound mainly has the following technical problems: 1) the expensive raw material, such as diiodine or dibromobicyclo[1,1,1]pentane, needs to be used, and the reaction yield is relatively low, and the conditions are harsh; 2) because the propellane is unstable under the alkaline condition, a traditional batch reaction may not be scaled up, and it may only be prepared on the small scale in the laboratory, the reaction is scaled up to 100 g, and the yield is significantly reduced to 60%; and 3) a process of dropwise adding the metal reagent in the batch reaction takes a long time and is dangerous in operation, for example, while the methyl lithium is used, the methane gas is produced during the reaction process, and the reaction temperature/pressure is difficult to control, and there is a great safety risk for scale-up.

Therefore, the development of a scalable process is a very promising and arduous task, and it is also a problem to be solved urgently in the synthesis of the propellane and the derivative thereof.

SUMMARY

The present disclosure aims to provide a method for continuously synthesizing a propellane compound, as to solve a technical problem in an existing technology that the synthesis yield of the propellane compound is low.

In order to achieve the above objective, according to one aspect of the present disclosure, a method for continuously synthesizing a propellane compound is provided. The method includes the following steps: 1,1-dibromo-2,2-chloromethylcyclopropane or a derivative thereof as a raw material to form a ring with a lithium metal agent by a continuous reaction, so as to synthesize the propellane compound.

Further, the 1,1-dibromo-2,2-chloromethylcyclopropane or the derivative thereof has the following structure:

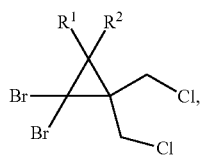

wherein $R^1$ and $R^2$ each represents hydrogen, alkyl, alkoxy, or aryl, the structures represented by $R^1$ and $R^2$ are the same or different, and $R^1$ and $R^2$ are preferably —$CH_3$ or —$C_2H_5$.

Further, the lithium metal agent is one selected from a group consisting of phenyl lithium, benzyl lithium, methyllithium, ethyllithium, butyllithium, isopropyllithium and dodecyl lithium.

Further, the temperature of the continuous reaction is −78~5° C.

Further, the method for continuously synthesizing the propellane compound further includes a continuous online quenching reaction after the continuous reaction is completed; preferably, a quencher used in the continuous online quenching reaction is aqueous ammonia; more preferably, the concentration of the aqueous ammonia is 0.5~3.0 g/g; and further preferably, the concentration of the aqueous ammonia is 1.0 g/g.

Further, the continuous reaction is carried out in a continuous stirred tank reactor; preferably, the continuous stirred tank reactor includes a first-stage continuous stirred tank reactor, a second-stage continuous stirred tank reactor, and a third-stage continuous stirred tank reactor that are connected in series; preferably, the 1,1-dibromo-2,2-chloromethylcyclopropane or the derivative thereof is dissolved in a first solvent to obtain solution A, and the lithium metal agent is dissolved in a second solvent to obtain solution B, the solution A and the solution B are added to the continuous stirred tank reactor for the continuous reaction by an automatic feeding system; and preferably, the first solvent and the second solvent are respectively one or more selected from a group consisting of n-pentane, n-hexane, n-heptane, n-butyl ether, diethyl ether and methyl tert-butyl ether.

Further, in the solution A, the molar concentration of the 1,1-dibromo-2,2-chloromethylcyclopropane or the derivative thereof is 0.5~3.0 M.

Further, in the solution B, the molar concentration of the lithium metal agent is 1.0~3.0 M.

Further, the feeding ratio of the solution A and the solution B is 1:2.0~1:3.0.

Further, the reaction temperature in the first-stage continuous stirred tank reactor is −51° C. to −75° C., and the reaction time is 20~40 min; preferably, the reaction temperature in the second-stage continuous stirred tank reactor is −5° C. to 5° C., and the reaction time is 30~60 min; and preferably, the reaction temperature in the third-stage continuous stirred tank reactor is −5° C. to 5° C., and the reaction time is 30~60 min.

A technical scheme of the present disclosure is applied, and a continuous reaction device is used. Continuous feeding, continuous reaction, continuous transfer, and continuous quenching are performed, and the post-treatment may even acquire a separation yield of more than 90%, so the efficient synthesis of the propellane is achieved. In addition, the continuous process is capable of shortening the reaction time, and solving a problem that a product in scale-up production is unstable under an alkaline condition and is deteriorated with the long reaction time; and the use of the continuous process greatly reduces a risk that the lithium reagent is used in the reaction, and it is more beneficial to the scale-up production.

DETAILED DESCRIPTION OF THE EMBODIMENTS

It should be noted that embodiments in the present disclosure and features in the embodiments may be combined with each other in the case without conflicting. The present disclosure is described in detail below in combination with the embodiments.

According to a typical embodiment of the present disclosure, a method for continuously synthesizing a propellane compound is provided. The method includes the following steps: 1,1-dibromo-2,2-chloromethylcyclopropane or a derivative thereof as a raw material to form a ring with a lithium metal agent by a continuous reaction, so as to synthesize the propellane compound.

A technical scheme of the present disclosure is applied, and a continuous reaction device is used. Continuous feeding, continuous reaction, continuous transfer, and continuous quenching are performed, and the post-treatment may even acquire a separation yield of more than 90%, so the efficient synthesis of the propellane is achieved. In addition, the continuous process is capable of shortening the reaction time, and solving a problem that a product in scale-up production is unstable under an alkaline condition and is deteriorated with the long reaction time; and the use of the continuous process greatly reduces a risk that the lithium reagent is used in the reaction, and it is more beneficial to the scale-up production.

Typically, in an embodiment of the present disclosure, 1,1-dibromo-2,2-chloromethylcyclopropane or the derivative thereof has the following structure:

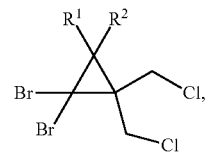

wherein $R^1$ and $R^2$ each represents hydrogen, alkyl, alkoxy, or aryl, the structures represented by $R^1$ and $R^2$ are the same or different, and $R^1$ and $R^2$ are preferably —$CH_3$ or —$C_2H_5$.

Preferably, the lithium metal agent is one selected from a group consisting of phenyl lithium, benzyl lithium, methyllithium, ethyllithium, butyllithium, isopropyllithium and dodecyl lithium. These lithium reagents have the characteristics of small metal ion radius, strong polarization ability, strong alkalinity and the like, and may more completely capture hydrogen or bromine. Preferably, the temperature of the continuous reaction is −78~5° C. In fact, the continuous reaction may be divided into three stages. The first stage of hydrogen extraction needs to be performed at a low temperature, and the lithium reagent may be destroyed at a high temperature; and the second stage and the third stage of the reactions need to be performed at about 0 degrees.

According to a typical embodiment of the present disclosure, the method for continuously synthesizing the propellane compound further includes a continuous online quenching reaction after the continuous reaction is completed; and it is convenient for the industrial continuous production. Preferably, a quencher used in the continuous online quenching reaction is aqueous ammonia; the concentration of the aqueous ammonia is 1.0~3.0 g/g; and more preferably, the concentration of the aqueous ammonia is 1.0 g/g.

In a typical embodiment of the present disclosure, the continuous reaction is performed in a continuous stirred tank reactor. Typically, the continuous stirred tank reactor includes a first-stage continuous stirred tank reactor, a second-stage continuous stirred tank reactor, and a third-stage continuous stirred tank reactor that are connected in series. In this way, it may be equivalent to several different reactor units which are connected together, and each reactor unit may have the different temperatures, reaction temperatures, raw material ratios and the like, it is more convenient for the flexible control of the reaction conditions.

In a typical embodiment of the present disclosure, the 1,1-dibromo-2,2-chloromethylcyclopropane or the derivative thereof is dissolved in a first solvent to obtain solution A, and the lithium metal agent is dissolved in a second solvent to obtain solution B, the solution A and the solution B are added to the continuous stirred tank reactor for the continuous reaction by an automatic feeding system, this operation is convenient to control the addition amount of the 1,1-dibromo-2,2-chloromethylcyclopropane or the derivative thereof and the lithium metal reagent. Preferably, the first solvent and the second solvent are respectively one or more selected from a group consisting of n-pentane, n-hexane, n-heptane, n-butyl ether, diethyl ether and methyl tert-butyl ether. These solvents are all inert solvents, have no special functional groups, and are stable, not easy to react, relatively cheap in price, and it is conducive to the control of the industrial production cost.

According to a typical embodiment of the present disclosure, in the solution A, the molar concentration of the 1,1-dibromo-2,2-chloromethylcyclopropane or the derivative thereof is 0.5~3.0 M; and in the solution B, the molar concentration of the lithium metal agent is 1.0~3.0 M. Reactants are fully used in this range. In order to make the reaction proceed fully, preferably, the feeding ratio (the mol ratio of a reaction substrate after conversion) of the solution A and the solution B is 1:2.0~1:3.0.

According to a typical embodiment of the present disclosure, the reaction temperature in the first-stage continuous stirred tank reactor is −75° C. to −51° C., for example, −74° C., −73° C., −71° C., −70° C., −68° C., −66° C.° C., −65° C., −64° C., −62° C., −60° C., −58° C., −56° C., −55° C., −54° C., and −52° C., and the reaction time is 20~40 min; preferably, the reaction temperature in the second-stage continuous stirred tank reactor is −5° C. to 5° C., for example, −5° C., −4° C., −3° C., −2° C., −1° C., 0° C., 1° C., 2° C., 3° C., 4° C. or 5° C., and the reaction time is 30~60 min; and preferably, the reaction temperature in the third-stage continuous stirred tank reactor is −5° C. to 5° C., for example, −5° C., −4° C., −3° C., −2° C., −1° C., 0° C., 1° C., 2° C., 3° C., 4° C. or 5° C., and the reaction time is 30~60 min. The reaction in the first-stage continuous stirred tank reactor belongs to a first-stage temperature-controlled dropwise-adding section, and a dropwise-adding process needs to be performed at a low temperature, otherwise, the raw material may be deteriorated; and the reactions in the second-stage continuous stirred tank reactor and the third-stage continuous stirred tank reactor belong to the second-stage and the third-stage which are reaction sections, after the dropwise-adding is completed, the reaction needs to be performed at about 0° C., so the temperature is controlled in the range of −5 to 5° C. The control of the above reaction time is because the dropwise-adding process releases heat apparently, within the controllable temperature range, the first-stage dropwise-adding section needs 20~40 min, the second-stage and the third-stage are the reaction time, the total time is 1~2 h, and the reactants may be converted completely.

The beneficial effects of the present disclosure are further described below in combination with the embodiments.

Contrast Example 1

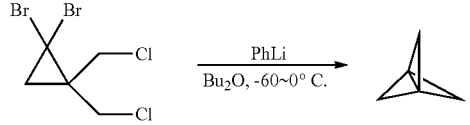

(1) Device specifications: a three-stage 1000 mL continuous stirred tank reactor (CSTR, namely a continuous stirred tank reactor), a 50 ml plunger pump, a 5000 g balance, and a 1.0 L feeding bottle.

(2) Raw material ratios:
Solution A: 5.0 kg 1,1-dibromo-2,2-chloromethylcyclopropane+2.0 vol n-butyl ether, and L1 (feed rate of solution A)=4.5 g/min.
Solution B: 2.2 eq phenyl lithium/n-butyl ether solution, and L2 (feed rate of solution B)=4.5 g/min.
Solution C: 1.0 g/g aqueous ammonia, and L3 (feed rate of solution C)=1.0 g/min.

(3) Reaction conditions: the three-stage CSTR is used, in a first-stage low-temperature section, the temperature is controlled to be −50~0° C., retention volume: 500 ml, in second-stage and third-stage reaction sections, the temperature is controlled to be 0° C., retention volume: 700 ml, it is overflowed to a receiving bottle in the third-stage, the temperature of the receiving bottle is controlled to be 0° C., the total retention volume is 1200 ml, and retention time (RT)=2.0 h. An automatic feeding system is opened, and fed by two materials, L1=4.5 g/min, L2=4.5 g/min, the two materials are mixed in the first-stage CSTR low-temperature section, after 40 min, it is overflowed to the second-stage and third-stage reaction sections for reaction, and after 70 min, the third-stage CSTR begins to overflow to the receiving bottle, and the feeding system is opened, L3=1.0 g/min, and the aqueous ammonia is continuously fed to quench the reaction. Post-treatment, liquid separation, and low-temperature distillation are performed to obtain 0.761 kg of a product (converted content), and the NMR yield is 68%.

Embodiment 1

Raw Material:

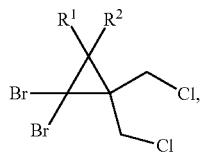

$R^1$=H, and $R^2$=CH$_3$

Solution A: 0.31 kg 1,1-dibromo-2,2-chloromethylcyclopropane+2.0 vol n-butyl ether.
Solution B: 2.2 eq phenyl lithium/n-butyl ether solution.
Solution C: 1.0 g/g aqueous ammonia.

Reaction conditions: the three-stage CSTR is used, in a first-stage low-temperature section, the temperature is controlled to be −65° C., retention volume: 50 ml, in second-stage and third-stage reaction sections, the temperature is controlled to be 0° C., retention volume: 70 ml, it is overflowed to a receiving bottle in the third-stage, the temperature of the receiving bottle is controlled to be 0° C., the total retention volume is 120 ml, and RT=2.0 h. An automatic feeding system is opened, and fed by two materials, L1=0.48 g/min, L2=0.40 g/min, the two materials are mixed in the first-stage CSTR low-temperature section, after 40 min, it is overflowed to the second-stage and third-stage reaction sections for reaction, and after 70 min, the third-stage CSTR begins to overflow to the receiving bottle, and the feeding system is opened, L3=0.1 g/min, and the aqueous ammonia is continuously fed to quench the reaction. Post-treatment, liquid separation, and low-temperature distillation are performed to obtain 70.5 g of a product (converted content), and the NMR yield is 85%.

Embodiment 2

Device specifications are the same as in Embodiment 1, and the differences from Embodiment 1 are as follows:
Raw material:

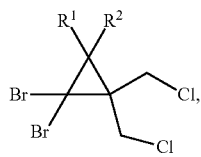

$R^1$=H, and $R^2$=C$_2$H$_5$

Solution A: 0.33 kg 1,1-dibromo-2,2-chloromethylcyclopropane+2.0 vol n-butyl ether.
Solution B: 2.2 eq phenyl lithium/n-butyl ether solution.
Solution C: 1.0 g/g aqueous ammonia.

Reaction conditions: the three-stage CSTR is used, in a first-stage low-temperature section, the temperature is controlled to be −65° C., retention volume: 50 ml, in second-stage and third-stage reaction sections, the temperature is controlled to be 0° C., retention volume: 70 ml, it is overflowed to a receiving bottle in the third-stage, the temperature of the receiving bottle is controlled to be 0° C., the total retention volume is 120 ml, and RT=2.0 h. An automatic feeding system is opened, and fed by two materials, L1=0.49 g/min, L2=0.40 g/min, the two materials are mixed in the first-stage CSTR low-temperature section, after 40 min, it is overflowed to the second-stage and third-stage reaction sections for reaction, and after 70 min, the third-stage CSTR begins to overflow to the receiving bottle, and the feeding system is opened, L3=0.1 g/min, and the aqueous ammonia is continuously fed to quench the reaction. Post-treatment, liquid separation, and low-temperature distillation are performed to obtain 84.70 g of a product (converted content), and the NMR yield is 90.06%.

Embodiment 3

Device specifications are the same as in Embodiment 1, and the differences from Embodiment 1 are as follows:
Methyl lithium is used as a lithium reagent.
Raw Material Ratio:
Solution A: 0.5 kg 1,1-dibromo-2,2-chloromethylcyclopropane+2.0 vol n-butyl ether.
Solution B: 2.2 eq methyl lithium/n-butyl ether solution.
Solution C: 1.0 g/g aqueous ammonia.

Reaction conditions: the three-stage CSTR is used, in a first-stage low-temperature section, the temperature is controlled to be −65° C., retention volume: 500 ml, in second-stage and third-stage reaction sections, the temperature is controlled to be 0° C., retention volume: 700 ml, it is overflowed to a receiving bottle in the third-stage, the temperature of the receiving bottle is controlled to be 0° C., the total retention volume is 1200 ml, and RT=2.0 h. An automatic feeding system is opened, and fed by two materials, L1=0.46 g/min, L2=0.43 g/min, the two materials are mixed in the first-stage CSTR low-temperature section, after 40 min, it is overflowed to the second-stage and third-stage reaction sections for reaction, and after 70 min, the third-stage CSTR begins to overflow to the receiving bottle, and the feeding system is opened, L3=0.1 g/min, and the aqueous ammonia is continuously fed to quench the reaction. Post-treatment, liquid separation, and low-temperature distillation are performed to obtain 92.67 g of a product (converted content), and the NMR yield is 86%.

Embodiment 4

Device specifications are the same as in Embodiment 1, and the differences from Embodiment 1 are as follows:
The reaction temperature in the first-stage is −51° C.
Raw Material Ratio:
Solution A: 0.5 kg 1,1-dibromo-2,2-chloromethylcyclopropane+2.0 vol n-butyl ether.
Solution B: 2.2 eq phenyl lithium/n-butyl ether solution.
Solution C: 1.0 g/g aqueous ammonia.

Reaction conditions: the three-stage CSTR is used, in a first-stage low-temperature section, the temperature is controlled to be −51° C., retention volume: 50 ml, in second-stage and third-stage reaction sections, the temperature is controlled to be 0° C., retention volume: 70 ml, it is overflowed to a receiving bottle in the third-stage, the temperature of the receiving bottle is controlled to be 0° C., the total retention volume is 120 ml, and RT=2.0 h. An automatic feeding system is opened, and fed by two materials, L1=0.46 g/min, L2=0.43 g/min, the two materials are mixed in the first-stage CSTR low-temperature section, after 40 min, it is overflowed to the second-stage and third-stage reaction sections for reaction, and after 70 min, the third-stage CSTR begins to overflow to the receiving bottle, and the feeding system is opened, L3=0.3 g/min, and the aqueous ammonia is continuously fed to quench the reaction. Post-treatment, liquid separation, and low-temperature distillation are performed to obtain 92.88 g of a product (converted content), and the NMR yield is 83%.

Embodiment 5

Device specifications are the same as in Embodiment 1, and the differences from Embodiment 1 are as follows.
The amount of aqueous ammonia is 3.0 g/g.
Raw Material Ratio:
Solution A: 0.5 kg 1,1-dibromo-2,2-chloromethylcyclopropane+2.0 vol n-butyl ether.
Solution B: 2.2 eq phenyl lithium/n-butyl ether solution.
Solution C: 3.0 g/g aqueous ammonia.
Reaction conditions: the three-stage CSTR is used, in a first-stage low-temperature section, the temperature is controlled to be −65° C., retention volume: 50 ml, in second-stage and third-stage reaction sections, the temperature is controlled to be 0° C., retention volume: 70 ml, it is overflowed to a receiving bottle in the third-stage, the temperature of the receiving bottle is controlled to be 0° C., the total retention volume is 120 ml, and RT=2.0 h. An automatic feeding system is opened, and fed by two materials, L1=0.46 g/min, L2=0.43 g/min, the two materials are mixed in the first-stage CSTR low-temperature section, after 40 min, it is overflowed to the second-stage and third-stage reaction sections for reaction, and after 70 min, the third-stage CSTR begins to overflow to the receiving bottle, and the feeding system is opened, L3=0.3 g/min, and the aqueous ammonia is continuously fed to quench the reaction. Post-treatment, liquid separation, and low-temperature distillation are performed to obtain 100.7 g of a product (converted content), and the NMR yield is 90%.

Embodiment 6

Device specifications are the same as in Embodiment 1, and the differences from Embodiment 1 are as follows.
N-hexane is used as a reaction solvent.
Raw Material Ratio:
Solution A: 0.5 kg 1,1-dibromo-2,2-chloromethylcyclopropane+2.0 vol n-butyl ether.
Solution B: 2.2 eq phenyl lithium/n-butyl ether solution.
Solution C: 1.0 g/g aqueous ammonia.
Reaction conditions: the three-stage CSTR is used, in a first-stage low-temperature section, the temperature is controlled to be −65° C., retention volume: 50 ml, in second-stage and third-stage reaction sections, the temperature is controlled to be 0° C., retention volume: 70 ml, it is overflowed to a receiving bottle in the third-stage, the temperature of the receiving bottle is controlled to be 0° C., the total retention volume is 120 ml, and RT=2.0 h. An automatic feeding system is opened, and fed by two materials, L1=0.44 g/min, L2=0.45 g/min, the two materials are mixed in the first-stage CSTR low-temperature section, after 40 min, it is overflowed to the second-stage and third-stage reaction sections for reaction, and after 70 min, the third-stage CSTR begins to overflow to the receiving bottle, and the feeding system is opened, L3=0.1 g/min, and the aqueous ammonia is continuously fed to quench the reaction. Post-treatment, liquid separation, and low-temperature distillation are performed to obtain 97.7 g of a product (converted content), and the NMR yield is 88%.

Embodiment 7

Device specifications are the same as in Embodiment 1, and the differences from Embodiment 1 are as follows.
The substrate concentration is changed, and 3.0 vol n-butyl ether is used.
Raw Material Ratio:
Solution A: 0.5 kg 1,1-dibromo-2,2-chloromethylcyclopropane+3.0 vol n-butyl ether.
Solution B: 2.2 eq phenyl lithium/n-butyl ether solution.
Solution C: 1.0 g/g aqueous ammonia.
Reaction conditions: the three-stage CSTR is used, in a first-stage low-temperature section, the temperature is controlled to be −65° C., retention volume: 50 ml, in second-stage and third-stage reaction sections, the temperature is controlled to be 0° C., retention volume: 70 ml, it is overflowed to a receiving bottle in the third-stage, the temperature of the receiving bottle is controlled to be 0° C., the total retention volume is 120 ml, and RT=2.0 h. An automatic feeding system is opened, and fed by two materials, L1=0.55 g/min, L2=0.33 g/min, the two materials are mixed in the first-stage CSTR low-temperature section, after 40 min, it is overflowed to the second-stage and third-stage reaction sections for reaction, and after 70 min, the third-stage CSTR begins to overflow to the receiving bottle, and the feeding system is opened, L3=0.1 g/min, and the aqueous ammonia is continuously fed to quench the reaction. Post-treatment, liquid separation, and low-temperature distillation are performed to obtain 95.5 g of a product (converted content), and the NMR yield is 86%.

Embodiment 8

Device specifications are the same as in Embodiment 1, and the differences from Embodiment 1 are as follows:
The ratio of solution A and solution B is changed to 1:3.0.
Raw Material Ratio:
Solution A: 0.5 kg 1,1-dibromo-2,2-chloromethylcyclopropane+2.0 vol n-butyl ether.
Solution B: 3.0 eq phenyl lithium/n-butyl ether solution.
Solution C: 1.0 g/g aqueous ammonia.
Reaction conditions: the three-stage CSTR is used, in a first-stage low-temperature section, the temperature is controlled to be −65° C., retention volume: 50 ml, in second-stage and third-stage reaction sections, the temperature is controlled to be 0° C., retention volume: 70 ml, it is overflowed to a receiving bottle in the third-stage, the temperature of the receiving bottle is controlled to be 0° C., the total retention volume is 120 ml, and RT=2.0 h. An automatic feeding system is opened, and fed by two materials, L1=0.38 g/min, L2=0.50 g/min, the two materials are mixed in the first-stage CSTR low-temperature section, after 40 min, it is overflowed to the second-stage and third-stage reaction sections for reaction, and after 70 min, the third-stage CSTR begins to overflow to the receiving bottle, and the feeding system is opened, L3=0.1 g/min, and the aqueous ammonia is continuously fed to quench the reaction. Post-treatment, liquid separation, and low-temperature distillation are performed to obtain 93.2 g of a product (converted content), and the NMR yield is 84%.

Embodiment 9

Device specifications are the same as in Embodiment 1, and the differences from Embodiment 1 are as follows.
The reaction time of each stage is changed.
Raw Material Ratio:
Solution A: 0.5 kg 1,1-dibromo-2,2-chloromethylcyclopropane+2.0 vol n-butyl ether.
Solution B: 2.2 eq phenyl lithium/n-butyl ether solution.
Solution C: 1.0 g/g aqueous ammonia.

Reaction conditions: the three-stage CSTR is used, in a first-stage low-temperature section, the temperature is controlled to be −65° C., retention volume: 50 ml, in second-stage and third-stage reaction sections, the temperature is controlled to be 0° C., retention volume: 70 ml, it is overflowed to a receiving bottle in the third-stage, the temperature of the receiving bottle is controlled to be 0° C., the total retention volume is 120 ml, and RT=2.0 h. An automatic feeding system is opened, and fed by two materials, L1=0.41 g/min, L2=0.50 g/min, the two materials are mixed in the first-stage CSTR low-temperature section, after 30 min, it is overflowed to the second-stage and third-stage reaction sections for reaction, and after 100 min, the third-stage CSTR begins to overflow to the receiving bottle, and the feeding system is opened, L3=0.1 g/min, and the aqueous ammonia is continuously fed to quench the reaction. Post-treatment, liquid separation, and low-temperature distillation are performed to obtain 100.9 g of a product (converted content), and the NMR yield is 91%.

Embodiment 10

Device specifications are the same as in Embodiment 1, and the differences from Embodiment 1 are as follows:
The reaction temperature of each stage is changed.
Raw Material Ratio:
Solution A: 0.5 kg 1,1-dibromo-2,2-chloromethylcyclopropane+2.0 vol n-butyl ether.
Solution B: 2.2 eq phenyl lithium/n-butyl ether solution.
Solution C: 1.0 g/g aqueous ammonia.
Reaction conditions: the three-stage CSTR is used, in a first-stage low-temperature section, the temperature is controlled to be −65° C., retention volume: 50 ml, in second-stage and third-stage reaction sections, the temperature is controlled to be 15° C., retention volume: 70 ml, it is overflowed to a receiving bottle in the third-stage, the temperature of the receiving bottle is controlled to be 15° C., the total retention volume is 120 ml, and RT=2.0 h. An automatic feeding system is opened, and fed by two materials, L1=0.41 g/min, L2=0.50 g/min, the two materials are mixed in the first-stage CSTR low-temperature section, after 40 min, it is overflowed to the second-stage and third-stage reaction sections for reaction, and after 70 min, the third-stage CSTR begins to overflow to the receiving bottle, and the feeding system is opened, L3=0.1 g/min, and the aqueous ammonia is continuously fed to quench the reaction. Post-treatment, liquid separation, and low-temperature distillation are performed to obtain 89.84 g of a product (converted content), and the NMR yield is 81%.

Embodiment 11

Device specifications and material parameters are all the same as in Embodiment 1, and the difference from Embodiment 1 is only that the reaction temperature in the first-stage is −55° C., and finally the NMR yield is 89.1%.

Embodiment 12

Device specifications and material parameters are all the same as in Embodiment 1, and the difference from Embodiment 1 is only that the reaction temperature in the first-stage is −70° C., and finally the NMR yield is 92.5%.

Embodiment 13

Device specifications and material parameters are all the same as in Embodiment 1, and the difference from Embodiment 1 is only that the reaction temperatures in the first-stage and the second-stage are −5° C., and finally the NMR yield is 81.7%.

Embodiment 14

Device specifications and material parameters are all the same as in Embodiment 1, and the difference from Embodiment 1 is only that the reaction temperature in the first-stage is 5° C., and finally the NMR yield is 83.1%.

Embodiment 15

Device specifications and material parameters are all the same as in Embodiment 1, and the difference from Embodiment 1 is only that the total reaction time of the second-stage and the third-stage is 60 min, and finally the NMR yield is 86.9%.

Embodiment 16

Device specifications and material parameters are all the same as in Embodiment 1, and the difference from Embodiment 1 is only that the total reaction time of the second-stage and the third-stage is 120 min, and finally the NMR yield is 91.2%.

It may be seen from the above descriptions that the above embodiments of the present disclosure achieve the following technical effects.

1) For the first time, the use of the continuous device is achieved, the 1,1-dibromo-2,2-chloromethylcyclopropane and the derivative thereof are used as the raw materials, through the continuous reaction, it is cycle-closed with the lithium metal agent to prepare the propellane compound.

2) The continuous reaction mode is capable of shortening the unit reaction time, and reducing the contact time between the product and the metal reagent, the damage of the product in the alkaline condition is reduced in the greatest degree. It is changed from the unable scale-up of the batch reaction to the continuous scale-up, and to the continuous high-efficiency scale-up, so the industrialized large-scale production of the propellane compound becomes possible.

3) The continuous process is capable of increasing the separation yield to 90% after the scale-up, and greatly reducing the synthesis cost of the product; and a problem that the modifications of many drugs at present may not be achieved due to the high price of the propellane derivative is solved. 4) The use of the continuous device is capable of reducing a risk factor of using the active metal reagent, and greatly saving the labor cost at the same time, and it is beneficial to the industrial scale-up production.

5) Compared to a traditional reaction, the continuous reaction may be stopped or terminated at any time according to the actual situation. The post-treatment may also be performed in batches or combined as needed, and it is convenient and simple.

The above are only preferred embodiments of the present disclosure, and are not used to limit the present disclosure. Various modifications and changes may be made to the present disclosure by those skilled in the art. Any modifications, equivalent replacements, improvements and the like made within the spirit and principle of the present disclosure should be included in a scope of protection of the present disclosure.

What claimed is:
1. A method for continuously synthesizing a propellane compound, wherein the method comprises the following step: using 1,1-dibromo-2,2-bis(chloromethyl)cyclopropane or a derivative thereof as a raw material to form a ring with a lithium metal agent by a continuous reaction, so as to synthesize the propellane compound;

the continuous reaction is carried out in a continuous stirred tank reactor; the continuous stirred tank reactor comprises a first-stage continuous stirred tank reactor, a second-stage continuous stirred tank reactor and a third-stage continuous stirred tank reactor which are connected in series; the 1,1-dibromo-2,2-bis(chloromethyl)cyclopropane or the derivative thereof is dissolved in a first solvent to obtain solution A, and the lithium metal agent is dissolved in a second solvent to obtain solution B, and the solution A and the solution B are added to the continuous stirred tank reactor by an automatic feeding system for the continuous reaction;

in the solution A, the molar concentration of the 1,1-dibromo-2,2-bis(chloromethyl) cyclopropane or the derivative thereof is 0.5 to 3.0 M;

in the solution B, the molar concentration of the lithium metal agent is 1.0 M to 3.0 M;

the feeding ratio of the solution A to the solution B is 1:2.0 to 1:3.0;

in the first stage continuous stirred tank reactor, the reaction temperature is −51° C. to −75° C., and the reaction time is 20 to 40 min;

in the second stage continuous stirred tank reactor, the reaction temperature is −5° C. to 5° C., and the reaction time is 30 to 60 min; and in the third stage continuous stirred tank reactor, the reaction temperature is −5° C. to 5° C., and the reaction time is 30 to 60 min;

the 1,1-dibromo-2,2-bis(chloromethyl)cyclopropane or a derivative thereof has the following structure:

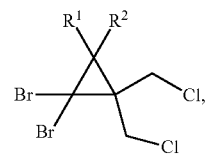

wherein $R^1$ and $R^2$ each independently are —$CH_3$ or —$C_2H_5$.

2. The method of claim 1, wherein the lithium metal agent is one selected
from a group consisting of phenyl lithium, benzyl lithium, methyllithium, ethyllithium, butyllithium, isopropyllithium and dodecyl lithium.

3. The method of claim 1, wherein the method for continuously synthesizing the propellane compound further comprises a continuous online quenching reaction after the continuous reaction is completed.

4. The method of claim 3, wherein a quencher used in the continuous online quenching reaction is aqueous ammonia.

5. The method of claim 4, wherein the concentration of the aqueous ammonia is 0.5 to 3.0 g/g.

6. The method of claim 5, wherein the concentration of the aqueous ammonia is 1.0 g/g.

7. The method of claim 1, wherein the first solvent and the second solvent are respectively one or more selected from a group consisting of n-pentane, n-hexane, n-heptane, n-butyl ether, ethyl ether and methyl tert-butyl ether.

* * * * *